United States Patent
Camden

(10) Patent No.: US 6,265,427 B1
(45) Date of Patent: Jul. 24, 2001

(54) PHARMACEUTICAL COMPOSITION FOR THE METHOD OF TREATING LEUKEMIA

(75) Inventor: James Berger Camden, West Chester, OH (US)

(73) Assignee: The Proctor & Gamble Company, Cincinnati, OH (US)

(*) Notice: Subject to any disclaimer, the term of this patent is extended or adjusted under 35 U.S.C. 154(b) by 0 days.

(21) Appl. No.: 09/375,173

(22) Filed: Aug. 16, 1999

Related U.S. Application Data

(63) Continuation-in-part of application No. 08/910,801, filed on Aug. 12, 1997, now abandoned, which is a continuation of application No. 08/473,817, filed on Jun. 7, 1995, now abandoned.

(51) Int. Cl.$^7$ ............................................... A61K 31/415
(52) U.S. Cl. ............................................................ 514/388
(58) Field of Search ............................................. 514/388

(56) References Cited

U.S. PATENT DOCUMENTS

| | | | |
|---|---|---|---|
| 3,010,968 | 11/1961 | Loux | 260/309.2 |
| 3,370,957 | 2/1968 | Wagner et al. | 99/90 |
| 3,499,761 | 3/1970 | Dersch . | |
| 3,541,213 | 11/1970 | Klopping | 424/273 |
| 3,669,969 | 6/1972 | Lunn | 260/256.4 |
| 3,738,995 | 6/1973 | Adams et al. | 260/309.2 |
| 3,881,014 | 4/1975 | Regel et al. | 424/273 |
| 3,956,262 | 5/1976 | Heyes et al. | 260/140 |
| 4,046,906 | 9/1977 | Frensch et al. | 424/273 |
| 4,731,366 | 3/1988 | Munro et al. | 514/278 |
| 4,814,329 | 3/1989 | Harsanyi et al. | 514/396 |
| 5,098,923 | 3/1992 | Karjalainen et al. | 514/396 |
| 5,114,951 | 5/1992 | King | 514/290 |
| 5,149,527 | 9/1992 | Weisenthal . | |
| 5,290,801 | 3/1994 | Higley et al. | 514/395 |
| 5,310,748 | 5/1994 | Wilde et al. | 514/395 |
| 5,329,012 | 7/1994 | Anderson | 548/318.5 |
| 5,364,875 | 11/1994 | Wilde | 514/375 |
| 5,434,163 | 7/1995 | Edlind et al. | 514/310 |
| 5,629,341 | 5/1997 | Camden . | |
| 5,656,615 | 8/1997 | Camden . | |
| 5,665,713 | 9/1997 | Camden . | |
| 5,665,751 | 9/1997 | Camden . | |
| 5,767,138 * | 6/1998 | Camden | 514/365 |

(List continued on next page.)

FOREIGN PATENT DOCUMENTS

| | | |
|---|---|---|
| 667158 | 11/1965 | (BE) . |
| 617968 | 10/1994 | (EP) . |
| 2155888 | 5/1973 | (FR) . |
| 7-277 956 | 10/1995 | (JP) . |
| WO 94/04541 | 3/1994 | (WO) . |
| WO 96/32103 | 10/1996 | (WO) . |
| WO 96/32104 | 10/1996 | (WO) . |
| WO 96/32107 | 10/1996 | (WO) . |
| WO 96/32115 | 10/1996 | (WO) . |
| WO 96/40119 | 12/1996 | (WO) . |
| WO 96/40120 | 12/1996 | (WO) . |
| WO 96/40122 | 12/1996 | (WO) . |
| WO 97/05870 | 2/1997 | (WO) . |
| WO 97/05872 | 2/1997 | (WO) . |
| WO 97/05873 | 2/1997 | (WO) . |
| WO 98/32440 | 2/1998 | (WO) . |
| WO 98/51303 | 11/1998 | (WO) . |
| WO 98/51304 | 11/1998 | (WO) . |
| WO 99/59585 | 11/1999 | (WO) . |

OTHER PUBLICATIONS

Chemical Abstracts 65:6570h referring to BE patent, (1965).
Brown, et al., J. Am. Chem. Soc., 83:1764–65 (1961).
Grenda, et al., J. Org. Chem. 30,259 (1965).
W. T. Thompson, Agricultural Chemicals Book IV, Fungicides, pp. 154, 121, 123; 1993–1994.
Carter, W.A. CRC Press, Selective Inhibitors of Viral Functions, pp. 277–346 (1975).
Merck Index, Eighth Edition, 1968, p. 1035.
DuPont, Material Safety Data Sheet Benlate Fungicide, Sep. 27, 1994.
Derwent Publications, AN 95–400884 and Japan Patent Abstracts, JP 07 277956; duplicate of above JP citation (1995).
Teicher, et al., Breast Cancer Research and Treatment, vol. 36, No. 2, pp. 227–236 (1995).

(List continued on next page.)

*Primary Examiner*—Jerome D. Goldberg
(74) *Attorney, Agent, or Firm*—Rose Ann Dabek; Steven W. Miller

(57) ABSTRACT

Method of treating leukemia, inhibiting the growth or proliferation of leukemic cells or extending the life span of a animal having leukemia are disclosed. The methods comprise the step of treating the leukemia with an effective amount of a compound of the Formula I

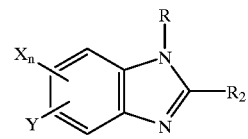

or a pharmaceutically acceptable salt or prodrug form thereof, wherein:

X is hydrogen, halogen or alkyl of less than 7 carbon atoms;

n is a positive integer of less than 4;

Y is hydrogen, chlorine, nitro, methyl or ethyl;

R is hydrogen or an alkyl group of from 1 to 8 carbon atoms, alkylcarbamyl;

$R_2$ is 4-thiazolyl or $NHCOOR_1$; and $R_1$ is an aliphatic hydrocarbon of less than 7 carbon atoms.

A chemotherapeutic agent and/or potentiator can be used in conjunction with the compound of the Formula I.

32 Claims, No Drawings

U.S. PATENT DOCUMENTS

| | | |
|---|---|---|
| 5,770,616 | 6/1998 | Camden . |
| 5,840,742 | 11/1998 | Camden . |
| 5,854,231 | 12/1998 | Camden . |
| 5,872,142 | 2/1999 | Camden . |
| 5,880,144 | 3/1999 | Camden . |
| 5,900,429 | 5/1999 | Camden . |
| 5,902,804 | 5/1999 | Camden . |
| 5,908,855 | 6/1999 | Camden . |
| 5,929,099 * | 7/1999 | Camden ............................... 514/365 |
| 5,932,604 | 8/1999 | Camden . |
| 5,932,609 | 8/1999 | Camden . |
| 6,025,377 | 2/2000 | Camden . |
| 6,077,862 | 6/2000 | Camden . |

OTHER PUBLICATIONS

Bissery, et al., Seminars in Oncology: Management of Breast Cancer: A New Therapeutic Approach, vol. 22, No. 6–S13, pp. 3–16, (1995).
Chemical Abstracts 113:112365 (1990) Ghannoum, et al.
Ram, et al., J. Med. Chem., 35, No. 3, 539–547 (1992).
Nene, et al., International Science Publisher, Fungicides in Plant Disease Control, Chapter 9, 1993.
Private Communication to Dr. Von Hoff from National Institute of Health, National Cancer Society (1995).
Chemical Abstracts 92:123231 (1979) Menzel et al.
Lacey et al., International Journal for Parasitology, vol. 18 No. 7, pp. 885–936 (1988).
Merck Index, $12^{12}$ ed., 7943 and 9877, Merck & Co. (NJ 1996).
Chemical Abstracts 102:217569 (1985) Elgebaly et al.
Chemical Abstracts 87:161659 (1997) Lundy et al.
Lacey, et al., Biochemical Pharma., vol. 34, No. 7, pp. 1073–1077 (1985).
Lassnau, et al., Chest, vol. 104, pp. 119–122 (1993).
Georgopapadakov et al., Science vol. 264, pp. 371–373 (Apr. 15, 1994).
Carter et al., Chemotherapy of Cancer, $2^{nd}$ Ed., John Wiley & Sons, NY, NY (1981), pp. 362–365.
Chemical Abstracts 98:66765, Vergieva; 1982.
Pending Application of Camden, Serial No. 09/264,942, filed Mar. 9, 1999. (5638D2C).
Pending Application of Camden, Serial No. 09/375,173, filed Aug. 16, 1999. (5702CR).
Pending Application of Camden, Serial No. 09/469,389, filed Dec. 22, 1999. (5703D2C).
Pending Application of Camden, Serial No. 09/360,499, filed Jul. 26, 1999. (5781D).
Pending Application of Camden, Serial No. 08/674,182, filed Jul. 16, 1996, CPA filed Feb. 10, 1999.
Pending Application of Camden, Serial No. 09/245,520, filed Feb. 5, 1999. (5782D).
Pending Application of Camden, Serial No. 09/220,914, filed Dec. 24, 1998. (5783C).
Pending Application of Camden,Serial No. 09/371,457, filed Aug. 10, 1999. (5784R).
Pending Application of Camden, Serial No. 09/371,459, filed Aug. 10, 1999. (5784R2).
Pending Application of Camden, Serial No. 09/364,021, filed Jul. 30, 1999. (5785D2).
Pending Application of Camden, Serial No. 09/408,664, filed Sep. 29, 1999. (5785D2R).
Pending Application of Camden, Serial No. 09/312,948, filed May 17, 1999. (5786D).
Pending Application of Camden, Serial No. 09/394,383, filed Sep. 10, 1999. (5786DR).
Pending Application of Camden, Serial No. 09/394,382, filed Sep. 10, 1999. (5786DR2).
Pending Application of Camden, Serial No. 09/218,884, filed Dec. 22, 1998. (6496D).
Pending Application of Camden, Serial No. 08/857,811, filed May 16, 1997, CPA filed Jul. 28, 1999. (6643).
Pending Application of Camden, Serial No. 09/312,949, filed May 17, 1999. (7161R).
Pending Application of Camden, Serial No. 09/374,717, filed Aug. 13, 1999. (7719).
Pending Application of Camden, Serial No. 09/552,408, filed Apr. 19, 2000. (6496D2).
Pending Application of Camden, Serial No. 09/552,825, filed Apr. 20, 2000. (6643D2).
Pending Application of Camden, Serial No. 09/552,820, filed Apr. 20, 2000. (6643D3).
Pending Application of Camden, Serial No. 09/560,059, filed Apr. 27, 2000. (5781D3).
Pending Application of Camden, Serial No. 09/603,040, filed Jun. 26, 2000. (5781DC).
Pending Application of Camden, Serial No. Not Yet Correctly Assigned, Assigned same SN as 8069, filed Apr. 28, 2000. (8068).
Pending Application of Camden, Serial No. Not Yet Correctly Assigned, Assigned same SN as 8068, filed Apr. 28, 2000. (8069).
Pending Application of Camden, Serial No. 09/602,170, filed Jun. 22, 2000. (5783C2).
Pending Application of Camden, Serial No. 09/603,322, filed Jun. 26, 2000. (5781D2).
Delatour et al., Therapie, vol. 31, No. 4., pp. 505–515, (1976), and translation thereof.
Elgebaly et al., J. Natl. Cancer Inst., vol. 74, No. 4, pp. 811–815 (1985).
Friedman, et al., Biochimica et Biophysica Acta, 544 (1978) pp. 605–614.
Lacey, et al., Biochemical Pharma, vol. 34, No. 19, pp. 3603–3605 (1985).
Chemical Abstracts 121:175012z, (1994) p. 607, Katiyar, et. al.
Stedman's Medical Dictionary, $24^{th}$ ed., 1983, pp. 777–778.
Aur, J. Pediatr., 78, No. 1, (1971) pp. 129–131.
Lundy et al., Cancer Treat. Rep., vol. 62, No. 11, (1978), pp. 1955–1962.
Lundy et al., Surg. Forum, vol. 27, No. 62 (1976) pp. 132–134.
Marinovich, et al., Toxicol., vol. 94, No. 1–3, (1994) pp. 173–185.
Lovett, Diss. Abstr. Int., (Sci), vol. 39, No. 11, (1979) pp. 5315–5316.
Brabender, et al., Cancer Research, vol. 36 (Mar., 1976) pp. 905–916.
Atassi et al., Europ., J. Cancer, vol. 11 (1975) pp. 599–607.
Lapras, M. et al. Bull. Soc. Sci. Vet. et Med. comparee, Lyon, 1975, vol. 77, No. 6, pp. 379–397 (in French)—and English translation thereof.

* cited by examiner

PHARMACEUTICAL COMPOSITION FOR THE METHOD OF TREATING LEUKEMIA

This is a continuation in part application of application Ser. No. 08/910,801 filed Aug. 12, 1997, now abandoned, which is a continuation of application Ser. No. 08/473,817 filed on Jun. 7, 1995 now abandoned. Each application is incorporated by reference herein.

TECHNICAL FIELD

This invention relates to a pharmaceutical composition for and a method of treating leukemia in mammals, wherein the composition comprises a benzimidazole derivative.

BACKGROUND OF THE INVENTION

Cancers, including leukemia, are the leading cause of death in animals and humans. The exact cause of many cancers is not known, but links between certain activities such as smoking or exposure to carcinogens and the incidence of certain types of carcinomas, lymphomas, e.g., leukemia and tumors, has been shown by a number of researchers.

Many types of chemotherapeutic agents have been shown to be effective against leukemia, but not all types of leukemia cells respond to these agents, and, unfortunately, many of these agents also destroy normal cells.

Despite advances in the field of leukemia treatments, the leading therapies to date are radiation, chemotherapy and bone marrow transplants. However, these therapies generally harm normal cells as well as leukemic cells. Ideally cytotoxic agents that have specificity for leukemia cells while only minimally affecting normal healthy cells would be extremely desirable. Unfortunately, none have been found and instead agents which target especially rapidly dividing cells (both diseased and normal) have been used.

SUMMARY OF THE INVENTION

The invention provides a method, and pharmaceutical composition therefor, of treating leukemia, inhibiting the growth or inhibiting the proliferation of leukemic cells while affecting little or no undesired side effects on normal cells, and extending the life span of a animal having leukemia. Accordingly, one aspect of the invention provides a method of treating leukemia in a animal comprising the step of administering to the animal a safe and effective amount of a compound of the Formula:

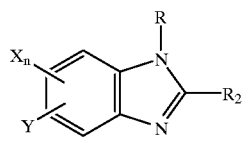

or a pharmaceutically acceptable salt or prodrug form thereof, wherein:

X is hydrogen, halogen, alkyl of less than 7 carbon atoms or alkoxy of less than 7 carbon atoms;

n is a positive integer of less than 4;

Y is hydrogen, chlorine, nitro, methyl or ethyl;

R is hydrogen or an alkyl group of from 1 to 8 carbon atoms; or alkylcarbamoyl wherein the alkyl group has from 3 to 6 carbon atoms;

$R_2$ is 4-thiazolyl or $NHCOOR_1$; and $R_1$ is an aliphatic hydrocarbon of less than 7 carbon atoms; and a pharmaceutically acceptable carrier.

Preferably the compositions are:

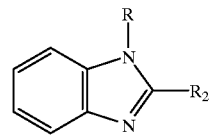

wherein R is an alkyl of 1 through 8 carbon atoms and $R_2$ is selected from the group consisting of 4-thiazolyl, $NHCOOR_1$, wherein $R_1$ is methyl, ethyl or isopropyl and the non-toxic, pharmaceutically acceptable acid addition salts with both organic and inorganic acids or prodrugs thereof.

$R_1$ is preferably an alkyl group of less than 7 carbon atoms. In other preferred embodiments, R is an alkyl of from 1 to 8 carbon atoms, and $R_1$ is methyl, ethyl or isopropyl. The most preferred compounds include those wherein Y is chloro and X is hydrogen and also 2-(4-thiazolyl) benzimidazole (thiabendazole), methyl(butylcarbamoyl)-2-benzimidazolecarbamate (benomyl) and 2-(methoxycarbonylamino)benzimidzole (carbendazim).

The compound of the Formula I is used alone or in combination with a potentiator or other chemotherapeutic agent to treat leukemia.

Another aspect of the invention provides a method of inhibiting the proliferation of leukemic cells in vitro, in vivo or ex vivo comprising the step of treating said cells with an effective amount of the compound of the Formula I, as defined above. Optionally, one or more potentiators and chemotherapeutic agents are used in combination with the compound of the Formula I to inhibit the proliferation of leukemic cells.

Yet another aspect of the invention provides a method of inhibiting the growth of leukemic cells in vitro, in vivo or ex vivo comprising the step of treating said cells with an effective amount of the compound of the Formula I, as defined above. Optionally, one or more potentiators and chemotherapeutic agents are used in combination with the compound of the Formula I to inhibit the growth of leukemic cells.

Still another aspect of the invention provides a method of extending the life span of a animal having leukemia comprising the step of administering to the animal an effective amount of the compound of the Formula I, as defined above, whereby the life span of the animal is extended beyond the expected life span of a comparable animal having a comparable degree of leukemia development not being treated with a compound of the Formula I. Optionally, one or more potentiators and chemotherapeutic agents are used in combination with the compound of the Formula I to extend the life span of the animal.

A further aspect of the invention provides a pharmaceutical composition for the treatment of leukemia in a animal comprising a pharmaceutically acceptable carrier, an effective amount of a compound of the Formula I, as defined above, and a safe and effective amount of one or more potentiators and other chemotherapeutic agents.

The pharmaceutical composition of the invention includes all known stereoisomers, enantiomers, regioisomers, stereoisomers, and diastereomers of the compound of the Formula I as well as pharmaceutically acceptable salts and prodrugs thereof.

The compounds of the invention are administered orally, rectally, topically, intravenously, or parenterally.

DETAILED DESCRIPTION OF THE INVENTION

A. Definitions

As used herein, "Formula I" refers to a benzimidazole having the general formula:

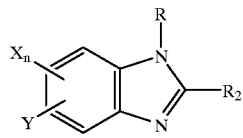

or a pharmaceutically acceptable salt or prodrug form thereof, wherein:

X is hydrogen, halogen, alkyl of less than 7 carbon atoms or alkoxy of less than 7 carbon atoms;

n is a positive integer of less than 4;

Y is hydrogen, chlorine, nitro, methyl or ethyl;

R is hydrogen or an alkyl group of from 1 to 8 carbon atoms; or alkylcarbamoyl wherein the alkyl group has from 3 to 6 carbon atoms;

$R_2$ is 4-thiazolyl or $NHCOOR_1$; and $R_1$ is an aliphatic hydrocarbon of less than 7 carbon atoms As used herein, a "pharmaceutically acceptable" component is one that is suitable for use with humans and/or animals without undue adverse side effects (such as toxicity, irritation, and allergic response) commensurate with a reasonable benefit/risk ratio. It is expected, however, that some side effects may be observed during treatment with a compound of the Formula I.

As used herein, the term "animal" includes any warm blooded animal and the preferred animals are mammals.

As used herein, the term "safe and effective amount" or "therapeutically effective amounts" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will vary with such factors as the particular condition being treated, the physical condition of the patient, the type of animal being treated, the duration of the treatment, the nature of concurrent therapy (if any), and the specific formulations employed and the stricture of the compounds or its derivatives.

As used herein, a "pharmaceutical addition salts" is salt of the anti-leukemia compound with an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, the term "prodrug" refers to a form of the compound of the Formula I that has minimal therapeutic activity until it is converted to its desired biologically active form. A prodrug is a compound having one or more functional groups or carriers covalently bound thereto which functional groups or carriers are removed from the compound to form the biologically active form. A prodrug of a compound of the Formula I is prepared by modifying one or more functional groups present in the compound with one or more masking groups in such a way that the masking groups are cleaved, either in vivo after administration or in vitro prior to administration to form the biologically active form. Prodrugs include compounds wherein one or more of the functional groups of the compound of the Formula I are bonded to one or more protecting groups that cleave to form the unprotected or derivatized compound of the Formula I. Exemplary protecting groups are disclosed in "Protective Groups in Organic Synthesis" (by Green & Wuts, 1999, 3$^{rd}$ Ed.); "Protecting Groups (Tieme Foundations Organic Chemistry Series N Group" (by Kocienskie; Tieme Medical Publishers; 1994), the relevant disclosures of which are hereby incorporated by reference.

"Prodrugs" are considered to be any covalently bonded carriers which release the active parent drug according to the formula of the benzimidazole derivatives described above in vivo when such prodrug is administered to an animal subject. Prodrugs of the benzimidazole compounds are prepared by modifying functional groups present in the compounds in such a way that the modifications are cleaved, either in routine manipulation or in vivo, to the parent compounds. Prodrugs include compounds wherein hydroxy, amine, or sulfhydryl groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the benzimidazole derivatives; phosphate esters, dimethylglycine esters, aminoalkylbenzyl esters, aminoalkyl esters and carboxyalkyl esters of alcohol and phenol functional groups in the benzimidazole derivatives; and the like.

As used herein, a "pharmaceutical carrier" is a pharmaceutically acceptable solvent, suspending agent or vehicle for delivering the compound of the Formula I to an animal or human. The carrier may be liquid or solid and is selected with the planned manner of administration in mind.

As used herein, "cancer" or "leukemia" refers to neoplastic diseases which attack normal healthy blood cells, or bone marrow which produces blood cells, which are found in animals. The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease, i.e., acute or chronic; (2) the type of cell involved; myeloid (myelogenous), lymphoid (lymphogenous), or monocytic; and (3) the increase or non-increase in the number abnormal cells in the blood- leukemic or aleukemic (subleukemic).

The P388 leukemia model described herein is widely accepted as being predictive of in vivo anti-leukemia activity. It is believed that compound that tests positive in the P388 assay will generally exhibit some level of anti-leukemia activity in vitro, ex vivo or in vivo. The level of anti-leukemia activity will depend upon the type of leukemia being treated. Accordingly, the present invention includes methods of treating leukemia, inhibiting the proliferation of leukemic cells, inhibiting the growth of leukemic cells or extending the life span of a animal having leukemia where the leukemia is selected from the group including acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, and undifferentiated cell leukemia.

As used herein, the term "susceptible to treatment" refers to a leukemia which can be treated with a compound of the Formula I according to the methods of the invention. For example, leukemia which is susceptible to treatment will respond favorably to chemotherapy with a compound of the Formula I. A favorable response would include prolongation of the life span of a animal having the leukemia, inhibition of the proliferation of leukemic cells, inhibition of a growth of leukemic cells, reduction in the rate of disease progression in the animal, remission or regression of the disease in the animal, and/or improvement in the quality of life of a animal having leukemia. A leukemia can be identified as being susceptible to treatment by following the method of example 3 described below.

The compounds of the Formula I are prepared according to the method described in U.S. Pat. No. 3,738,995 issued to Adams et al., Jun. 12, 1973. The thiazolyl derivatives are prepared according to the method described in Brown et al. (*J. Am. Chem. Soc.* (1961), 83, 1764), and Grenda et al. (*J. Org. Chem.* (1965), 30, 259). Some of these compouds are also commercially available from BASF, Hoechst, E. I. Du Pont de Nemours, and MSD-Agvet. One skilled in the art of organic synthesis can easily determine methods to make the compounds of Formula I.

B. Adjunct Therapy

As used herein, "adjunct therapy" means that the patient in need of the drug is treated or given another drug for the disease and/or a potentiator in conjunction with the compound of the Formula I. This adjunct therapy can be sequential therapy where the patient is treated first with one compound and then the other within a given time period or concommitant therapy where the two compounds are administered substantially simultaneously or in overlapping dosing regimens.

The compound of the Formula I generally is used in single or multiple treatments. Alternatively, the compound of the Formula I is combined with other therapeutic agents, chemotherapeutic agents or potentiators to treat disorders. "Potentiators" are materials which affect the body's response or diseased cell's response to the compound of the Formula I. A "potentiator" can be any material which improves or increases the efficacy of a pharmaceutical composition containing the compound of the Formula I or acts as an immunomodulator to increase the efficacy of the compound of the Formula I.

In some embodiments of the invention, the compound of the Formula I is used in combination with one or more other anti-inflammatory, anti-viral, anti-fungal, amoebicidal, trichomonocidal, analgesic, anti-neoplastic, anti-hypertensives, anti-microbial and/or steroid drugs to treat leukemia and optionally another ongoing disease or disorder. An exemplary potentiator is triprolidine or its cis-isomer which are used in combination with chemotherapeutic agents and a compound of the Formula I. Triprolidine is described in U.S. Pat. No. 5,114,951 (1992). Another potentiator is procodazole, 1H-Benzimidazole-2-propanoic acid; [β-(2-benzimidazole) propionic acid; 2-(2-carboxyethyl) benzimidazole; propazol]. Procodazole is a non-specific immunoprotective agent active against viral and bacterial infections that is used with the compositions claimed herein. It is effective with a compound of the Formula I in the methods of the invention. Procodazole can also be combined with a compound of the Formula I and other chemotherapeutic agents and used in the method of the invention.

Other potentiators which can be used with a compound of the Formula I, and optionally another chemotherapeutic agent, in the methods of the invention include macrophage colony-stimulating factor (M-CSF), 7-thia-8-oxoguanosine, 6-mercaptopurine, vitamin A (retinol), and other known anti-tumor potentiators which can be used in conjunction with the compounds of Formula I include, monensin, an anti-sense inhibitor of the RAD51 gene, bromodeoxyuridine, dipyridamole, indomethacin, a monoclonal antibody, an anti-transferrin receptor immunotoxin, metoclopramide, N-solanesyl-N,N'-bis(3,4-dimethoxybelizyl)ethylenediamine, leucovorin, heparin, N-[4-[(4-fluorphenyl)sulfonly]phenyl] acetamide, heparin sulfate, cimetidine, a radiosensitizer, a chemosensitizer, a hypoxic cell cytotoxic agent, muramyl dipeptide, vitamin A, 2'-deoxycoformycin, a bis-diketopiperazine derivative, and dimethyl sulfoxide other anti-tumor potentiators.

The chemotherapeutic agents which can be used with a compound of the Formula I and an optional potentiator are generally grouped as DNA-interactive Agents, Antimetabolites, Tubulin-Interactive Agents, Hormonal agents and others such as Asparaginase or hydroxyurea. Each of the groups of chemotherapeutic agents can be further divided by type of activity or compound. For a detailed discussion of chemotherapeutic agents and their method of administration, see Dorr, et al, *Cancer Chemotherapy Handbook,* 2d edition, pages 15–34, Appleton & Lange (Connecticut, 1994) the disclosure of which is hereby incorporated by reference.

DNA-Interactive Agents include the alkylating agents, e.g. Cisplatin, Cyclophosphamide, Altretamine; the DNA strand-breakage agents, such as Bleomycin; the intercalating topoisomerase II inhibitors, e.g., Dactinomycin and Doxorubicin); the nonintercalating topoisomerase II inhibitors such as, Etoposide and Teniposide; and the DNA minor groove binder Plicamycin.

The alkylating agents form covalent chemical adducts with cellular DNA, RNA, and protein molecules and with smaller amino acids, glutathione and similar chemicals. Generally, these alkylating agents react with a nucleophilic atom in a cellular constituent, such as an amino, carboxyl, phosphate, sulfhydryl group in nucleic acids, proteins, amino acids, or glutathione. The mechanism and the role of these alkylating agents in cancer therapy is not well understood. Typical alkylating agents include:

Nitrogen mustards, such as Chlorambucil, Cyclophosphamide, Isofamide, Mechlorethamine, Melphalan, Uracil mustard;

Aziridine such as Thiotepa;

methanesulphonate esters such as Busulfan;

nitroso ureas, such as Carmustine, Lomustine, Streptozocin;

platinum complexes, such as Cisplatin, Carboplatin;

bioreductive alkylator, such as Mitomycin, and Procarbazine, Dacarbazine and Altretamine.

DNA strand breaking agents include Bleomycin.

DNA topoisomerase II inhibitors include the following:

Intercalators, such as Amsacrine, Dactinomycin, Daunorubicin, Doxorubicin, Idarubicin, and Mitoxantrone; and nonintercalators, such as Etoposide and Teniposide.

The DNA minor groove binder is Plicamycin.

The antimetabolites interfere with the production of nucleic acids by one or the other of two major mechanisms. Some of the drugs inhibit production of the deoxyribonucleoside triphosphates that are the immediate precursors for DNA synthesis, thus inhibiting DNA replication. Some of the compounds are sufficiently like purines or pyrimidines to be able to substitute for them in the anabolic nucleotide pathways. These analogs can then be substituted into the DNA and RNA instead of their normal counterparts. The antimetabolites useful herein include:

folate antagonists such as Methotrexate and trimetrexate pyrimidine antagonists, such as Fluorouracil, Fluorodeoxyuridine, CB3717, Azacitidine and Floxuridine purine antagonists such as Mercaptopurine, 6-Thioguanine, Pentostatin;

sugar modified analogs such as Cytarabine and Fludarabine; and ribonucleotide reductase inhibitors such as hydroxyurea.

Tubulin Interactive agents act by binding to specific sites on tubulin, a protein that polymerizes to form cellular microtubules. Microtubules are critical cell structure units. When the interactive agents bind on the protein, the cell can not form microtubules Tubulin Interactive agents include colchicine, Vincristine and Vinblastine, both alkaloids and Paclitaxel and cytoxan.

Hormonal agents are also useful in the treatment of cancers and tumors. They are used in hormonally susceptible tumors and are usually derived from natural sources. These include:

estrogens, conjugated estrogens and Ethinyl Estradiol and Diethylstilbesterol, Chlortrianisen and Idenestrol;

progestins such as Hydroxyprogesterone caproate, Medroxyprogesterone, and Megestrol; and androgens such as testosterone, testosterone propionate; fluoxymesterone, methyltestosterone.

Adrenal corticosteroids are derived from natural adrenal cortisol or hydrocortisone. They are used because of their anti inflammatory benefits as well as the ability of some to inhibit mitotic divisions and to halt DNA synthesis. These compounds include, Prednisone, Dexamethasone, Methylprednisolone, and Prednisolone.

Leutinizing hormone releasing hormone agents or gonadotropin-releasing hormone antagonists are used primarily the treatment of prostate cancer. These include leuprolide acetate and goserelin acetate. They prevent the biosynthesis of steroids in the testes.

Antihormonal antigens include:

antiestrogenic agents such as Tamoxifen, antiandrogen agents such as Flutamide; and antiadrenal agents such as Mitotane and Aminoglutethimide.

Hydroxyurea, which appears to act primarily through inhibition of the enzyme ribonucleotide reductase, can also be used in combination with the compound of the Formula I.

Asparaginase is an enzyme which converts asparagine to nonfunctional aspartic acid and thus blocks protein synthesis in the tumor. Asparaginase can also be used in combination with the compound of the Formula I to treat cancer.

Other chemotherapeutic benzimidazoles and griseofulvin can also be used in combination with the compound of the Formula I and optionally a potentiator to treat or inhibit the growth of cancer or extend the life span of a animal having cancer.

The amount and identity of a chemotherapeutic agent that is used with a compound of the Formula I in the methods of the invention will vary according to cellular response, patient response and physiology, type and severity of side effects, the disease being treated, the preferred dosing regimen, patient prognosis or other such factors.

The compound of the Formula I can be used in combination with one or more other agents or combination of agents known to possess anti-leukemia activity including, by way of example, α-interferon; interleukin-2; cytarabine and mitoxantrone; cytarabine and daunorubicin and 6-thioguanine; cyclophosphamide and 2-chloro-2'-deoxyadenosine; VP-16 and cytarabine and idorubicin or mitoxantrone; fludarabine and cytarabine and γ-CSF; chlorambucil; cyclophosphamide and vincristine and (prednisolone or prednisone) and optionally doxorubicin; tyrosine kinase inhibitor; and antibody; glutamine; clofibric acid; all-trans retinoic acid; ginseng diyne analog; KRN8602 (anthracycline drug); temozolomide and poly(ADP-ribose) polymerase inhibitors; lysofylline; cytosine arabinoside; chlythorax and elemental enteral diet enriched with medium-chain triglycerides; amifostine; gilvusmycin; or a hot water extract of the bark of *Acer nikoense*.

The compound of the Formula I can also be used in combination with other non-chemotherapeutic treatments for leukemia including bone marrow transplant, therapeutic apheresis, and radiation.

When a compound of the Formula I is used in combination with other therapeutic agents, the ratio of the compound of the Formula I to the other therapeutic agent will be varied as needed according to the desired therapeutic effect, the observed side-effects of the combination, or other such considerations known to those of ordinary skill in the medical arts. Generally, the ratio of the compound of the Formula I to other therapeutic agent will range from about 0.5%:99.5% wt. to about 99.5%:0.5% wt. Preferably from 1%:99% wt. to about 50%:50% wt. When the compound of the Formula I is administered before or after other therapeutic agents to treat viral infections, cancer, tumors, or other diseases, the respective doses and the dosing regimen of the compound of the Formula I and the other therapeutic agent may vary. The adjunct therapy can be sequential, that is the treatment with one agent first and then the second agent, or it can be concomitant treatment wherein two or more agents are administered substantially at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

For example, a full dosing regimen of the compound of the Formula I can be administered either before or after a full dosing regimen of the other therapeutic agent, or alternating doses of the compound of the Formula I and the other therapeutic agent may be administered. As a further example, the compound of the Formula I can be administered concomitantly with the other therapeutic agent.

Propionic acid and its salts and esters can also be used in combination with the pharmaceutical compositions claimed herein. Antioxidant vitamins such as vitamins A, C and E and beta-carotene can be added to these compositions.

C. Dosage and Delivery Forms

Any suitable dosage may be given in the method of the invention. The type of compound and the carrier and the amount will vary widely depending on the species of the warm blooded mammal, body weight, or the type of leukemia being treated. Generally a dosage of between about 2 milligram (mg) per kilogram (kg) of body weight and about 10000 mg per kg of body weight is suitable for the compound of the Formula I. Preferably from 150 mg to about 8000 mg/kg of body weight is used.

A dosage unit may comprise a single compound or mixtures thereof with other compounds or other cancer inhibiting compounds. The dosage unit can also comprise diluents, extenders, carriers, liposomes and the like. The unit may be in solid or gel form such as pills, tablets, capsules and the like or in liquid form suitable for oral, rectal, topical, intravenous injection or parenteral administration or injection into or around the bone marrow.

The dosage for the chemotherapeutic agent can be from about 1 mg to about 1000 mg/kg and will be the same as or less than the dosage normally used for that agent.

The range and ratio of the compound of the Formula I to chemotherapeutic agent will depend on the type of cancer or tumor being treated and the particular chemotherapeutic agent. Generally the range of dosage for the chemotherapeutic agent will the same as or lower than that used when the chemotherapeutic agent is used alone. The ratio of the compound of the Formula I to the chemotherapeutic agent will generally be in the range of about 1000:1 to 10:1, and preferably in the range of about 800:1 to 100:1 on a weight basis. Generally, about 500 mg to 5000 mg of the compound of the Formula I/kg of body weight is administered when about 0.5 to about 40 mg of the chemotherapeutic/kg of body weight is administered.

Any range of doses can be used. Generally the compound of the Formula I can be administered on a daily basis one or more times a day, or the compound of the Formula I can be given once to four times a week either in a single dose or separate doses during the day. Twice weekly dosing over a period of several weeks is preferred. However, the dosage and the dosage regimen will vary depending on the ability of the patient to sustain the desired and effective plasma levels of the the compound of the Formula I in the blood.

The identity of the chemotherapeutic agent, the pharmaceutical carrier and the amount of compound administered will vary widely depending on the species and body weight of mammal and the type of leukemia being treated. The dosage administered will vary depending upon known factors, such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

The compound of the Formula I, the potentiator and the chemotherapeutic agent are administered together in a single dosage form or separately in two or more different dosage forms. These can be administered independently by the same route or by two or more different routes of administration depending on the dosage forms employed.

The compound of the Formula I is preferably micronized or powdered so that it is more easily dispersed and solubilized by the body. Processes for grinding or pulverizing drugs are well known in the art. For example, a hammer mill or similar milling device are used.

Dosage forms (compositions) suitable for internal administration contain from about 1.0 milligram to about 5000 milligrams of active ingredient per unit. In these pharmaceutical compositions, the active ingredient will ordinarily be present in an amount of about 0.5 to about 95% by weight based on the total weight of the composition. Based on the body weight of the patient, the dosage may be administered in one or more doses several times per day or per week. Multiple dosage units may be required to achieve a therapeutically effective amount. For example, if the dosage form is 1000 mg, and the patient weighs 40 kg, one pill will provide a dose of 25 mg per kg for that patient. It will provide a dose of only 12.5 mg/kg for a 80 kg patient.

The compound of the Formula I has exhibited efficacy in vivo against leukemia in mice at doses of about 1000, 2000 and 4000mg/kg. Generally, an effective dose in mice is about 12 times the expected effective dose in humans. By way of general guidance, for humans a dosage of as little as about 2 milligrams (mg) per kilogram (kg) of body weight and up to about 10,000 mg per kg of body weight is suitable as a therapeutically effective dose. Preferably, from about 150 mg/kg to about 5,000 mg/kg of body weight is used. Other preferred doses range between 100 mg/kg to about 3000 mg/kg of body weight. However, a dosage of between about 2 milligrams (mg) per kilogram (kg) of body weight to about 400 mg per kg of body weight is also suitable for treating some forms of leukemia.

Suitable pharmaceutical compositions and dosage forms will preferably comprise the compound of the Formula I, a potentiator and optionally a chemotherapeutic agent. The ratio of the compound of the Formula I to potentiator is generally in the range of about 1000:1 to 1:1, and preferably 500:1 to 10:1 on a weight basis. When a chemotherapeutic agent is also present, the ratio of the compound of the Formula I to potentiator to chemotherapeutic agent is generally in the range of about 1000:1:1 to about 1:1:1, and preferably500:1:1 to about 300:1:10.

Generally about 2 to 1000 mg of the compound of the Formula I per kg of body weight is administered when about 2 to 500 mg of potentiator/kg of body weight and about 0.5 to 100 mg of chemotherapeutic agent/kg of body weight are administered.

Intravenously, the most preferred rates of administration may range from about 1 to about 1000 mg/kg/minute during a constant rate infusion. The compound of the Formula I may be administered in a single daily dose, or the total daily dosage may be administered in divided doses of two, three, or four times daily. The compound of the Formula I is generally given in one or more doses on a daily basis or from one to three times a week.

The compound of the Formula I is administered by any conventional means available for use in conjunction with pharmaceuticals, either as individual therapeutic agents or in combination with other therapeutic agents A dosage unit may comprise a single compound or mixtures thereof with other anti-cancer compounds, other cancer or tumor growth inhibiting compounds. The compound of the Formula I can be administered in oral dosage forms as tablets, capsules, pills, powders, granules, elixirs, tinctures, suspensions, syrups, and emulsions. The compound of the Formula I may also be administered in intravenous (bolus or infusion), intraperitoneal, subcutaneous, or intramuscular form, all using dosage forms well known to those of ordinary skill in the pharmaceutical arts.

The compound of the Formula I is typically administered in admixture with suitable pharmaceutical diluents, extenders, excipients, or carriers (collectively referred to herein as a pharmaceutically acceptable carrier or carrier materials) suitably selected with respect to the intended form of administration and as consistent with conventional pharmaceutical practices. The unit will be in a form suitable for oral, rectal, topical, intravenous injection or parenteral administration.

The compound of the Formula I can be administered alone but is generally mixed with a pharmaceutically acceptable carrier. This carrier can be a solid or liquid, and the type of carrier is generally chosen based on the type of administration being used.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modem Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers : Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.), the disclosures of which are hereby incorporated by reference.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like.

Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compound of the Formula I can also be administered in the form of liposome delivery systems, such as small unilamellar vesicles, large unilamallar vesicles, and multi-lamellar vesicles. Liposomes can be formed from a variety of phospholipids, such as cholesterol, stearylamine, or phosphatidylcholines.

The compound of the Formula I may also be coupled to soluble polymers as targetable drug carriers or as a prodrug. Such polymers include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compound of the Formula I may be coupled to a class of biodegradable polymers useful in achieving controlled release of a drug, for example, polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacylates, and crosslinked or amphipathic block copolymers of hydrogels.

The active ingredient can be administered orally in solid dosage forms, such as capsules, tablets, and powders, or in liquid dosage forms, such as elixirs, syrups, and suspensions. It can also be administered parentally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compound of the Formula I may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittant throughout the dosage regimen.

Parenteral and intravenous forms may also include minerals and other materials to make them compatible with the type of injection or delivery system chosen.

Useful pharmaceutical dosage forms for administration of the compound of the Formula I are illustrated as follows:

Capsules

A large number of unit capsules are prepared by filling standard two-piece hard gelatin capsules each with 100 to 500 milligrams of powdered active ingredient, 5–150 milligrams of lactose, 5–50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100–500 milligrams of the active ingredient. The capsules are washed and dried.

Tablets

A large number of tablets are prepared by conventional procedures so that the dosage unit was 100–500 milligrams of active ingredient, 0.2 milligrams of colloidal silicon dioxide, 5 milligrams of magnesium stearate, 50–275 milligrams of microcrystalline cellulose, 11 milligrams of starch and 98.8 milligrams of lactose. Appropriate coatings may be applied to increase palatability or delay absorption.

Injectable solution

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

The present invention also includes pharmaceutical kits useful, for example, for the treatment of cancer, which comprise one or more containers containing a pharmaceutical composition comprising a therapeutically effective amount of the compound of the Formula I. Such kits may further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, may also be included in the kit. It should be understood that although the specified materials and conditions are important in practicing the invention, unspecified materials and conditions are not excluded so long as they do not prevent the benefits of the invention from being realized.

The chemotherapeutic agents, the compound of the Formula I and, optionally, the potentiators are typically mixed with a pharmaceutically acceptable carrier. This carrier can be a solid or liquid and the type is generally chosen based on the type of administration being used. The active agent can be coadministered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms would also include minerals and other materials to make them compatible with the type of injection or delivery system chosen.

The compound of the Formula I is generally safe. The $LD_{50}$ is 50,000 mg/kg when given orally in a mouse. There are generally no special handling requirements. The compound of the Formula I can be given orally, and as it is not very water soluble, it is preferably given in tablet form or as a suspension.

D. Method of Treatment

The method of treatment can be any suitable method which is effective in the treatment of the particular cancer or tumor type being treated. Treatment may be oral, rectal, topical, parenteral or intravenous administration or by injection into the tumor or cancer. The method of applying an effective amount also varies depending on the disorder being treated. It is believed that parenteral treatment by intravenous, subcutaneous, or intramuscular application of the the compound of the Formula I, formulated with an appropriate carrier, additional cancer inhibiting compound or compounds or diluent to facilitate application will be the preferred method of administering the compounds to warm blooded animals.

In addition to the use of chemotherapeutic agents and potentiators, the compound of the Formula I can be combined with other therapeutic agents. Preferred adjuvants include griseofulvin, fluoconazole, glyphosate and propicodazole. The dosage level of these compounds when used in conjunction with the compound of the Formula I will be from about 150 mg/kg to about 6000 mg/kg.

The following examples illustrate the utility of the compound of the Formula I as an anti-leukemia agent.

EXAMPLE 1

Carbendazim in a P388 in vivo Study

Mice were randomly selected and divided into five groups of ten mice each: Group 1—a control group receiving canola oil but no drug treatment; Group 2—a treatment group receiving 125 mg of cytoxan (2-[bis(2-chloroethyl)-amino-1-oxo-2-aza-5-oxophosphoridin) per kg of body weight; Group 3—a treatment group receiving 4000 mg of carbendazim per kg of body weight; Group 4—a treatment group receiving 2500 mg of carbendazim per kg of body weight; and Group 5—a treatment group receiving 1000 mg of carbendazim per kg of body weight. The five groups were infected with leukemia [P388]. The diseased animals were dosed for five days, off two days, dosed again for another five days and off again for three days. Even with this irregular dosing regimen, positive results were noted. Of the ten mice in Group 1, one died after eight days, eight died after ten days, and all ten were dead after eleven days after infection with leukemia. Of the ten mice in Group 2, none died up to twenty one days after infection with leukemia. Of the ten mice in Group 3, one died on day fourteen, two each died on days 15, 16 and 17 and one each died on days 20, 21, and 22 after infection with leukemia. The mean number of survival days is 17.3 for Group 3. Of the ten mice in Group 4, two died on day fourteen, four died on day 15, 1 on day 16, 2 on day 19 and one on day 21 after infection with leukemia. The mean number of survival days is 16.5 for Group 4. Of the ten mice in Group 5, two each died on days 12, 13, 14, and 15, and one each died on days 16 and 17 after infection with leukemia. The mean number of survival days is 14.1 for Group 5.

Accordingly, carbendazim, a compound of the Formula I, is effective at extending the life span of a mammal having leukemia.

EXAMPLE 2

Carbendazim (A Compound of the Formula I) In Combination Griseofulvin

In in vivo mouse study for leukemia (P388), carbendazim (2-methoxycarbonylaminobenzimidazole) was tested in combination with griseofulvin. Cytoxan was the positive control at 300 mg/kg (qd×1) and had no deaths during the test period. The results are tabulated below:

| Dose mg/kg Griseofulvin | dose mg/kg carbendazim | % increase in survival time versus nontreated control |
|---|---|---|
| 0 | 3000 | 176 |
| 3000 | 3000 | 93 |
| 4000 | 3000 | 0 |
| 5000 | 3000 | 0 |
| 0 | 2000 | 190 |
| 3000 | 2000 | 186 |
| 4000 | 2000 | 157 |
| 5000 | 2000 | 0 |
| 0 | 1000 | 153 |
| 3000 | 1000 | 187 |
| 4000 | 1000 | 183 |
| 5000 | 1000 | 166 |
| 0 | 0 | 100 (control) |
| 3000 | 0 | 130 |
| 4000 | 0 | 165 |
| 5000 | 0 | 213 |

Accordingly, griseofalvin in combination with carbendazim is useful in extending the life span of a warm-blooded mammal having leukemia. Further, a composition comprising therapeutically effective amounts of carbendazim, a compound of the Formula I, and griseofulvin is useful for the treatment of leukemia in warm-blooded mammals and especially for extending the life span of warm-blooded mammals having leukemia. For example, when the combination of carbendazim and griseofulvin is administered at a total of 5,000 mg/kg or less, the survival rate of mice having leukemia is increased. As a further example, when the ratio of griseofulvin to carbendazim is 5 to 1 or less, the survival time of mice having leukemia is increased.

EXAMPLE 3

Determining if a Leukemia is Susceptible to Treatment

This example describes a general method for determining whether or not a particular type of leukemia is susceptible to treatment. Blood or bone marrow containing leukemic cells is obtained from a mammal and divided into two aliquots: a first control aliquot and a second test aliquot. An initial count of the leukemic cells is taken. The leukemic cells, which have been isolated and resuspended in a solution or which are present in the sampled blood, are exposed to a sufficient amount of the compound of the Formula I (usually 0.01 mg–10 mg/mL of solution) for a sufficient period of time (usually 8–72 hours) to inhibit the growth of, inhibit the proliferation of or lyse the leukemic cells. The control aliquot is not exposed to the compound of the Formula I. A final count of the leukemic cells in each aliquot is taken and compared. A solution containing leukemia that is susceptible to treatment with a compound of the Formula I will have a lower leukemic cell count after treatment than does the control aliquot.

What is claimed is:

1. A method of treating leukemia susceptible to treatment in an animal comprising the step of administering to the animal a composition comprising a pharmaceutically acceptable carrier and a safe and effective amount of a compound of the Formula I:

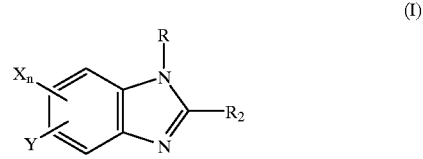

wherein:

X is hydrogen or halogen;

n is a positive integer of less than 4;

Y is hydrogen, chloro, nitro, methyl, or ethyl;

R is hydrogen, an alkyl group of from 1 to 8 carbon atoms, or alkylcarbamoyl wherein the alkyl group has from 3 to 6 carbon atoms;

$R_2$ is $NHCOOR_1$; and $R_1$ is an aliphatic hydrocarbon of less than 7 carbon atoms.

2. A method according to claim 1, wherein $R_1$ is an alkyl group of less than 7 carbon atoms.

3. A method according to claim 1, wherein R is hydrogen, an alkyl of from 1 to 8 carbon atoms, butylcarbamoyl, or isobutylcarbamoyl; and $R_1$ is methyl, ethyl, or isopropyl.

4. A method according to claim 1, wherein Y is chloro and X is hydrogen.

5. A method according to claim 1 wherein the compound of formula I is in the form of a pharmaceutically acceptable salt thereof.

6. A method according to claim 5 wherein said pharmaceutically acceptable salt is an acid addition salt of chloride.

7. A method according to claim 1 wherein the compound of formula I is present in an amount of from 2 mg/kg of body weight to 10,000 mg/kg of body weight.

8. The method of claim 1 wherein the compound of Formula I is 2-(methoxycarbonylamino)benzimidazole.

9. A method according to claim 8 wherein the compound of formula I is in the form of a pharmaceutically acceptable salt of 2-(methoxycarbonylamino)benzimidazole.

10. A method according to claim 9 wherein said pharmaceutically acceptable salt is an acid addition salt of chloride.

11. A method according to claim 8 wherein the 2-(methoxycarbonylamino)benzimidazole is present in an amount of from 2 mg/kg of body weight to 10,000 mg/kg of body weight.

12. A method according to claim 1 wherein said pharmaceutically acceptable carrier is in the form of an injectable solution.

13. A method of inhibiting the growth or proliferation of leukemic cells in vitro, in vivo or ex vivo comprising the step of treating said cells with an effective amount of a compound of the Formula I:

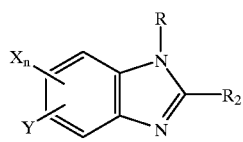 (I)

wherein:

X is hydrogen or halogen;

n is a positive integer of less than 4;

Y is hydrogen, chloro, nitro, methyl, or ethyl;

R is hydrogen, an alkyl group of from 1 to 8 carbon atoms, or alkylcarbamoyl wherein the alkyl group has from 3 to 6 carbon atoms;

$R_2$ is $NHCOOR_1$; and $R_1$ is an aliphatic hydrocarbon of less than 7 carbon atoms.

14. A method according to claim 13, wherein $R_1$ is an alkyl group of less than 7 carbon atoms.

15. A method according to claim 13, wherein R is hydrogen, an alkyl of from 1 to 8 carbon atoms, butylcarbamoyl, or isobutylcarbamoyl; and $R_1$ is methyl, ethyl, or isopropyl.

16. A method according to claim 13 wherein the compound of formula I is in the form of a pharmaceutically acceptable salt thereof.

17. A method according to claim 16 wherein said pharmaceutically acceptable salt is an acid addition salt of chloride.

18. A method according to claim 13 wherein the compound of formula I is present in an amount of from 2 mg/kg of body weight to 10,000 mg/kg of body weight.

19. The method of claim 13 wherein the compound of Formula I is 2-(methoxycarbonylamino)benzimidazole.

20. A method according to claim 19 wherein the compound of formula I is in the form of a pharmaceutically acceptable salt of 2-(methoxycarbonylamino) benzimidazole.

21. A method according to claim 20 wherein said pharmaceutically acceptable salt is an acid addition salt of chloride.

22. A method according to claim 19 wherein the 2-(methoxycarbonylamino)benzimidazole is present in an amount of from 2 mg/kg of body weight to 10,000 mg/kg of body weight.

23. A method of extending the life span of an animal having leukemia comprising the step of administering to the animal a safe and effective amount of a compound of the Formula I:

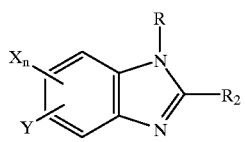 (I)

wherein:

X is hydrogen or halogen;

n is a positive integer of less than 4;

Y is hydrogen, chloro, nitro, methyl, or ethyl;

R is hydrogen, an alkyl group of from 1 to 8 carbon atoms, or alkylcarbamoyl wherein the alkyl group has from 3 to 6 carbon atoms;

$R_2$ is $NHCOOR_1$; and $R_1$ is an aliphatic hydrocarbon of less than 7 carbon atoms;

whereby the life span of the animal is extended beyond the expected life span of a comparable animal having a comparable degree of leukemia development not being treated with a compound of the Formula I.

24. A method according to claim 23, wherein $R_1$ is an alkyl group of less than 7 carbon atoms.

25. A method according to claim 23, wherein R is hydrogen, an alkyl of from 1 to 8 carbon atoms, butylcarbamoyl, or isobutylcarbamoyl; and $R_1$ is methyl, ethyl, or isopropyl.

26. A method according to claim 23 wherein the compound of formula I is in the form of a pharmaceutically acceptable salt thereof.

27. A method according to claim 26 wherein said pharmaceutically acceptable salt is an acid addition salt of chloride.

28. A method according to claim 23 wherein the compound of formula I is present in an amount of from 2 mg/kg of body weight to 10,000 mg/kg of body weight.

29. The method of claim 23 wherein the compound of Formula I is 2-(methoxycarbonylamino)benzimidazole.

30. A method according to claim 29 wherein the compound of formula I is in the form of a pharmaceutically acceptable salt of 2-(methoxycarbonylamino) benzimidazole.

31. A method according to claim 30 wherein said pharmaceutically acceptable salt is an acid addition salt of chloride.

32. A method according to claim 29 wherein the 2-(methoxycarbonylamino)benzimidazole is present in an amount of from 2 mg/kg of body weight to 10,000 mg/kg of body weight.

* * * * *